United States Patent [19]

Richard et al.

[11] Patent Number: 5,976,426

[45] Date of Patent: *Nov. 2, 1999

[54] LATEX OF CALIBRATED MONODISPERSE MAGNETIZABLE MICROSPHERES, PROCESS OF PREPARATION AND USE OF THE SAID LATEX IN CHEMISTRY OR IN BIOLOGY

[75] Inventors: Joël Richard, Longué ; Sophie Vaslin, Bry sur Marne, both of France

[73] Assignee: Societe Prolabo, Fontenay-Sous-Bois, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/793,352

[22] PCT Filed: Jun. 20, 1996

[86] PCT No.: PCT/FR96/00957

§ 371 Date: Feb. 24, 1997

§ 102(e) Date: Feb. 24, 1997

[87] PCT Pub. No.: WO97/00896

PCT Pub. Date: Jan. 9, 1997

[30] Foreign Application Priority Data

Jun. 22, 1995 [FR] France .................................. 95 07486

[51] Int. Cl.⁶ ....................................................... C08F 2/44
[52] U.S. Cl. ...................... 264/4.7; 252/62.54 ; 252/62.55
[58] Field of Search .................... 428/402.22; 252/62.54, 252/62.55; 264/4.7

[56] References Cited

U.S. PATENT DOCUMENTS

| | | | |
|---|---|---|---|
| 4,358,388 | 11/1982 | Daniel et al. ........................ | 252/62.54 |
| 4,421,660 | 12/1983 | Solc Nee Hajna .................. | 252/62.54 |
| 4,707,523 | 11/1987 | Chang et al. ........................... | 525/372 |
| 4,929,662 | 5/1990 | Hogenmuller et al. ................. | 524/376 |
| 4,983,311 | 1/1991 | Nakamura et al. .................. | 252/62.54 |
| 5,242,964 | 9/1993 | Bibette et al. ........................... | 524/376 |
| 5,275,901 | 1/1994 | Anno et al. ........................... | 430/106.6 |
| 5,356,713 | 10/1994 | Charmot et al. ........................ | 428/407 |

OTHER PUBLICATIONS

Richard rt al, CAPLUS AN 1994:606282, abstracting FR2691969.

Cannon, CA AN 103:62502, abstracting JP 60031148, 1985.

West 1.0 Abstract JP61215602 A, 1986.

*Primary Examiner*—Jeffrey C. Mullis
*Attorney, Agent, or Firm*—Jacobson, Price, Holman & Stern, PLLC

[57] ABSTRACT

Latices of monodisperse magnetizable microspheres contain a hydrophobic polymer matrix and magnetizable fillers. The microspheres have a calibrated particle-size distribution and a size of around 0.1–5 micrometers, and the polymer matrix, produced by a dispersion polymerization method, includes polymer chains derived from at least one vinyl monomer. The latices are useful in biology, in particular, for diagnostic and affinity chromatography methods.

13 Claims, 4 Drawing Sheets

5,976,426

LATEX OF CALIBRATED MONODISPERSE MAGNETIZABLE MICROSPHERES, PROCESS OF PREPARATION AND USE OF THE SAID LATEX IN CHEMISTRY OR IN BIOLOGY

The present invention relates to new latices of magnetizable microspheres formed by a hydrophobic polymer matrix and magnetizable fillers.

It also relates to a process for the preparation of the said latices and to the application of these latices in biology, especially in diagnostic methods, in affinity chromatography, as carrier for nucleic acid probes, and in chemistry.

Magnetic latices are aqueous dispersions of microspheres including a polymer matrix and magnetizable fillers which impart magnetic, especially superparamagnetic, properties to these microspheres.

It will be briefly recalled that, besides paramagnetic and ferromagnetic fillers, there is a third category of fillers called superparamagnetic fillers, which are characterized by the fact that they do not remain magnetic in the absence of a magnetic field and that these fillers have a magnetic magnetization that is nearly as high as that of ferromagnetic fillers.

In most cases these are iron oxides such as magnetite, hematite or ferrite when they have a particle size smaller than a certain critical limit.

Under the influence of a magnetic field the magnetizable microspheres are drawn toward the magnet and as a result can be rapidly separated from the aqueous phase.

This separation is reversible since, in the absence of magnetic field, the microspheres lose their magnetization and redisperse spontaneously. The size of the microspheres is generally between a few tens of nanometers and several microns.

The high specific surface due to their small size can be advantageously exploited in applications of immunological type using the antigen antibody reaction. The magnetic latex acts as a support that will allow the quantitative determination of the species present in the medium after separation.

The separation and washing stages are in this case greatly simplified by virtue of the use of these magnetizable microspheres.

To this day the processes utilized, especially those resulting in the magnetic latices marketed under the trade name Estapor®, rely on microsuspension polymerization mechanisms.

U.S. Pat. No. 4,339,337 makes it possible to prepare magnetizable microspheres of diameter ranging from 0.05 to 3 millimeters by suspension polymerization of a vinylaromatic monomer in the presence of one organosoluble initiator, of a dispersing agent and of a magnetizable filler dispersed within a solution of a water-insoluble polymer in the said monomer. The microspheres obtained enclose magnetizable fillers distributed in the polymer matrix.

In U.S. Pat. No. 4,358,388 it has also been proposed to prepare latices of magnetizable hydrophobic polymers by homogenization of an aqueous solution of emulsifier and of a dispersion of a magnetizable filler in an organic phase made up of an organosoluble initiator, of all or part of the hydrophobic monomer and/or of a water-insoluble organic compound, followed by polymerization. The latices obtained are made up of polymer microspheres from approximately 0.03 to 5 micrometers in diameter, enclosing magnetizable fillers distributed in the polymer matrix.

In suspension polymerization the monomer is dispersed in the form of droplets (size between 100 and 10,000 micrometers and 0.05 to 5 micrometers in the microsuspension) in the aqueous phase. The initiator is soluble in the organic phase and the suspension is maintained by mechanical stirring and addition of stabilizer (organic or inorganic colloid in the case of the conventional suspension, emulsifier in microsuspension). Each monomer droplet is considered to be a minireactor in which the polymerization kinetics are those of the bulk polymerization. They make it possible to obtain microspheres with a relatively broad particle size distribution in conventional suspension and a very polydisperse latex in the case of the microsuspension.

The latices obtained by the processes described in the prior art consequently produce very broad particle size distributions (typically from a few tens of microns to several microns). However, the effectiveness of the utilization of the magnetizable microspheres as carrier for immunological reagent is better insofar as the magnetic separation will be faster. This speed is a direct function of the homogeneity of the microspheres and in particular it increases when their particle size distribution narrows down.

Calibrated monodisperse magnetic microspheres would make it possible to obtain rapid and homogeneous phase separations. In addition, the monodispersity and the size calibration would make it possible to gain access precisely to the actual adsorption surface of the microspheres and hence to the theoretical binding capacity of the latter with regard to the reactive species.

A subject-matter of the present invention is to propose novel latices of magnetizable and calibrated microspheres while exhibiting a size larger than 0.05 micrometers in general.

Another subject-matter of the present invention is to propose a process for the preparation of latices of magnetizable microspheres which is simple and rapid, producing latices according to the invention in a single stage.

Another subject-matter of the present invention relates to the application of the latices according to the invention in biology, especially in diagnostic methods, and in chemistry.

Figure 1:
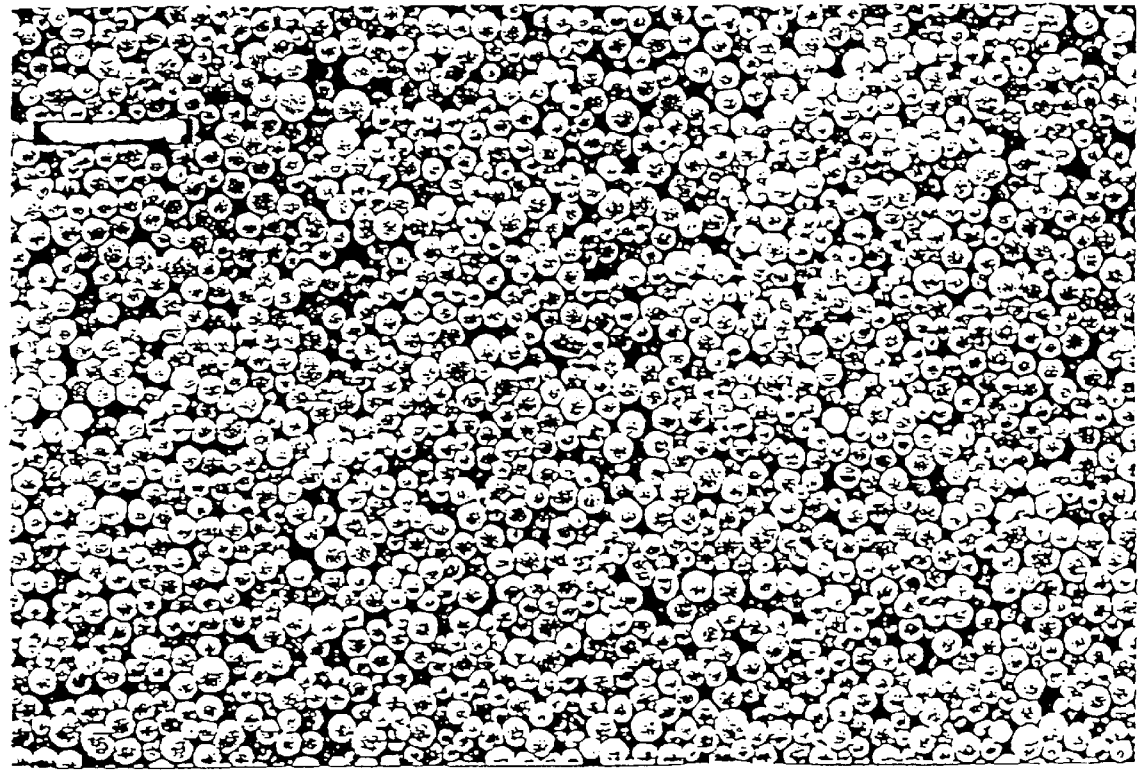
FIGS. 1–4 are photographs of magnified microspheres of the invention.

In the first place, the latex of magnetizable microspheres is characterized in that the microspheres have a calibrated particle size distribution, a size of between approximately 0.05 and 15 micrometers, and in that the polymer matrix is made up of polymers derived from at least one vinyl monomer, as obtained by the dispersion polymerization process.

The term "polymer matrix" is intended to mean that the magnetizable fillers are at least partially embedded in this matrix, it being possible for the residual part to be situated at the surface of the microsphere.

The expression "calibrated particle size distribution" is intended to mean that this distribution has a standard deviation smaller than or equal to 15%, preferably smaller than or equal to 10% and advantageously smaller than or equal to 5%; this means that ⅔ by weight of the microspheres have a diameter of between $d_m-\sigma$ and $d_m+\sigma$ ($d_m$: mean diameter, $\sigma$: standard deviation), in the case of a Gaussian distribution.

A number of other structural criteria also distinguish the microspheres according to the invention from those of the prior art.

The microspheres are additionally characterized in that they include a protective colloid, as will be described below.

The presence of a protective colloid at the surface and/or within the thickness of the polymer matrix gives the microspheres an increased stability to high ionic forces (stearic and possibly electrostatic stabilization).

Furthermore, at equal size, they sediment more slowly than the microspheres obtained by suspension or emulsion polymerization methods.

In addition, the dispersion polymerization process makes it possible to obtain polymer matrices forming microspheres in which the chains generally have an average (weight-, number- or Z-) molecular mass lower than that of the chains obtained by other processes, either in emulsion or in suspension.

A particularly advantageous dispersion polymerization process will be described hereinafter.

The magnetizable fillers preferably include a surface layer, monomolecular in most cases, of a water-insoluble dispersing agent.

These fillers are therefore in the form of a magnetic fluid called a "ferrofluid", cf. Kaiser and Miskolczy, J. Appl. Phys. 41 3 1064 (1970). A ferrofluid is a dispersion of very fine magnetic fillers which are preserved from any agglomeration by Brownian motion.

To prevent any agglomeration of the fillers as a result of the van der Waals attractive forces, the fillers are coated as indicated above. When a magnetic field is applied the magnetic force is transmitted to the entire volume of liquid and the ferrofluid responds like a fluid, namely that magnetic charges are not separated from their medium.

Among the dispersing agents forming a water-insoluble monomolecular coating around the magnetizable fillers there may be mentioned those which have a long hydrocarbon chain ending in a polar group of the —COOH or $NH_2$ type, and the like, such as fatty acids, fatty amines, etc., containing at least 12 carbon atoms and more particularly the $C_{18}$ fatty acids such as oleic, linoleic and linolenic acids.

The magnetizable fillers coated with dispersing agents can be prepared, for example, by peptization in the dispersing agent of magnetic fillers obtained by a sol-gel route, dispersion in an organic carrier liquid (U.S. Pat. No. 3,843,540) and then flocculation with the aid of a polar solvent of the ketone, ester or alcohol type and separation of the coated fillers.

The expression "vinyl monomer" is intended to mean any monomers which have an ethylenic double bond capable of allowing polymerization. These are therefore vinyl aromatic monomers among which styrene, alpha-methylstyrene, ethylstyrene, ethylvinylbenzene, tert-butylstyrene, vinyltoluene, chlorostyrene, bromostyrene and divinylbenzene may be mentioned. They will also be vinyl monomers which have an electrophilic group, such as vinyl acetate, vinyl chloride or acrylic derivatives such as especially $C_1$–$C_{12}$-alkyl acrylates or methacrylates, optionally hydroxylated, like hydroxyalkyl acrylates or methacrylates, acrylic or methacrylic acid or the amides of these, like acrylamide, and diacrylic derivatives or their esters or their anhydrides, like maleic anhydride. Dienes such as isoprene and butadiene can also be employed, especially as comonomers. The polymer chains are homopolymers or random or blocked copolymers or terpolymers derived from these vinyl monomers.

The magnetizable fillers preferably represent, approximately, 0.5 to 50% by weight of the weight of the said magnetizable microspheres. This proportion will be advantageously higher than 10%.

The magnetizable microspheres preferably have a size smaller than 10 micrometers, advantageously between approximately 0.1 and 5 micrometers and preferably between 0.5 micrometers and 2.5 micrometers.

The monomer is preferably chosen from the group consisting of styrene or styrene derivatives, alkyl acrylates or methacrylates, (the alkyl radicals preferably have between 1 and 10 carbon atoms, advantageously 1 to 5), acrylic or methacrylic acid, vinyl chloride, vinyl acetate, butadiene and isoprene.

The polymer obtained is advantageously chosen from the group consisting of polystyrene, polyalkyl methacrylate or polyalkyl acrylate or random or blocked copolymers of styrene and of alkyl acrylate or methacrylate.

The invention also relates to a process for the preparation of a monodisperse magnetic latex according to the invention, by dispersion polymerization, characterized in that an organic solution including at least one polymerizable vinyl monomer, an organic solvent, magnetizable fillers in the form of ferrofluid and a stabilizing system for the polymer formed, is reacted in the presence of an organosoluble polymerization initiator and in that the said magnetic latex is recovered.

Dispersion polymerization is a well-known process, simple and in only one stage, making it possible to prepare monodisperse latex microspheres. This technique is distinguished from suspension or microsuspension polymerization in the initial homogeneity of the polymerization medium. The distinctive characteristic of dispersion polymerization is due to the fact that the dispersant medium and the composition of the monomer/dispersant mixture are chosen such that the monomer is soluble in the dispersant medium while the polymer formed is not.

In other words, the monomer is soluble in the nonaqueous reaction medium while the polymer is insoluble.

The initiator is also soluble in the medium and, in order to stabilize the polymer microspheres formed, a steric stabilization, charged or otherwise, system (protective colloid) is employed.

A representation of the mechanism of dispersion polymerization may be given in broad outline, without this representation being capable of restricting in any way the scope of the present invention At the beginning of the polymerization the monomer, the stabilizing system and the initiator form, with the dispersant medium, a homogeneous solution which constitutes the continuous phase.

The initiator is decomposed thermally and the free radicals formed react with the monomer in solution to form growing soluble oligomer radicals.

When the oligomers have reached a critical chain length, they precipitate to form primary microspheres which are stabilized by adsorption and/or grafting of the protective colloid. These formed nuclei absorb the monomer from the continuous phase and the polymerization then continues within the microspheres swollen with monomers until the latter is exhausted.

In some aspects this type of polymerization is related both to emulsion polymerization with formation of nuclei, following the precipitation of growing chains in the homogeneous phase (Fitch's mechanism) and to polymerization in solution with an organosoluble initiator.

This technique makes it possible to prepare, in a single stage and very simply, calibrated monodisperse microspheres up to 15 micrometers in diameter, by virtue of a judicious adjustment of the operating conditions (temperature, stabilizer, initiator, etc.) etc.

To arrive at calibrated monodisperse final microspheres, the following conditions must be fulfilled:
the nucleation stage must be rapid so that all the nuclei are formed simultaneously.

all the oligomer radicals generated in the continuous phase during the period of growth of the microspheres must be captured by the existing microspheres before reaching the critical size for precipitation, which would give rise to the formation of new microspheres, the coalescence between the microspheres during the growth stage must be avoided.

According to one embodiment the initiator is dissolved in the monomer and the ferrofluid is added (solution A). The stabilizing system is then dissolved in the solvent (solution B). Solution B is heated to a temperature of approximately 40 to 80° C., generally in the region of 60° C., and then, after a determined period, solution A is added.

The polymerization is performed for a period of several hours, depending on the starting mixture.

The microspheres are then redispersed in water after the application of a magnetic field and then replacement of the supernatant with distilled water to which 0.5% of SDS (sodium lauryl sulfate) has optionally been added.

The microspheres are characterized by their diameter, their iron content and, in the case where the dispersant is based on a fatty acid, by the number of carboxyl functional groups.

The choice of the solvent depends on the nature of the ferrofluid, of the monomer and of the other reactants, in order that the solvent may become a non-solvent for the polymer as soon as the latter reaches a critical size.

In addition, during the precipitation of the oligomers, the magnetizable material must not be excluded from the disperse phase and must be localized within the microspheres.

Alcohols or mixtures of alcohols like methanol, ethanol, isopropanol, butanol and 2-methylpropanol, alkyl ethers like diethyl ether or methyl ethyl ether or alcohol-water or ether-alcohol mixtures will be especially mentioned among the polar solvents.

Aliphatic hydrocarbon solvents like cyclohexane and hexane will be especially mentioned among the apolar solvents.

Polar solvents are preferred to apolar solvents because they enable a much wider range of vinyl monomers to be employed.

When the solvent is a polar solvent, the monomers employed individually or as a mixture will be chosen preferably from the group consisting of vinylaromatic monomers such as styrene, styrene derivatives (vinyltoluene, ethylvinylbenzene, bromostyrene, chlorostyrene, alpha-methylstyrene, ethylstyrene and the like), acrylic derivatives such as acrylic and methacrylic acid, alkyl acrylates and methacrylates in which the alkyl group has from one to ten carbon atoms, hydroxyalkyl acrylates or methacrylates, acrylamide or methacrylamide, which make it possible to functionalize the surface of the microspheres and to adjust their hydrophilicity, vinyl monomers containing an attracting group such as esters of ethylenic acid containing 4 or 5 carbon atoms, vinyl chloride and dienes like butadiene and isoprene.

According to an advantageous alternative form, the invention relates to a latex in which the microspheres are functionalized by surface groups among which the carboxyl, amino, chloro, chloromethyl, sulfonate, sulfate, hydroxyl and thiol radicals may be mentioned.

In this case the protective colloid is advantageously a polymer chosen from the group consisting of poly(vinyl pyrrolidone), acrylic or methacrylic homopolymers, random or block copolymers of monomers chosen from the group consisting of, on the one hand, styrene or styrene derivatives and butadiene, on the other hand of methacrylic acid and acrylic acid, cellulose derivatives like hydroxypropyl cellulose, polyethylene oxides, the monoesters of the polymer of maleic anhydride, and the polymer of maleic acid. They are preferably poly(vinyl pyrrolidone) or a polyacrylate or methacrylate. The protective colloid generally also contributes to the introduction of functionalized groups at the surface of the microspheres.

When the solvent is an apolar solvent, especially hydrocarbon solvents like hexane or cyclohexane, the monomers are chosen especially from the group consisting of alkyl acrylates, $C_1$–$C_{12}$-alkyl methacrylates and styrene derivatives and dienes.

The stabilizing system is a polymer chosen from the group consisting of polyacrylates or methacrylates, block or random copolymers of monomers chosen from the group consisting of, on the one hand, olefins such as isobutylene, butylene, styrene derivatives, butadiene and butadiene derivatives like isoprene and vinyl esters and, on the other hand, acrylate or methacrylate derivatives and alkylsiloxanes. Styrene-butadiene-styrene or styrene-butadiene block copolymers may be employed in particular.

The polymerization initiator is preferably chosen from the group consisting of AIBN or 2,2'-azobis(isobutyronitrile), ACPA or 4,4'-azobis(4-cyanopentanoic acid), AMBN or 2,2'-azobis(2-methylbutyronitrile), BP or benzoyl peroxide and ADVN or 2,2'-azobis(2,4-dimethylvaleronitrile).

In all cases the solution preferably includes an ionic costabilizer such as a sodium dioctylsulfosuccinate (Aerosol OT®). Other costabilizers may also be suitable, such as methyltricaprylammonium chloride.

Colloidal additives like, for example, silica may also be added to the reaction mixture (latex) in order to reduce the viscosity of the mixture.

According to a preferred alternative form the process of preparation is characterized in that the solution includes, in part by weight:

| | |
|---|---|
| organic solvent | 45 to 90 |
| monomer | 5 to 30 |
| ferrofluid | 2 to 30 |
| stabilizing system | 2 to 10 |
| costabilizer | 0.1 to 1 |
| initiator | 0.1 to 1 |

Owing to the functional groups which are optionally present on the protective colloid, the magnetizable microspheres have the advantage of being functionalized in a known manner. The polar functional groups with or without a reactive group facilitate the subsequent association with biological molecules such as the antibodies. In the case where the functional groups have a reactive group, grafting with the molecule concerned, especially biological, will be referred to.

Furthermore, proteins can also be bound onto the surface either by passive adsorption or preferably by covalent bonding by means of carboxyl groups when the latter are present.

The invention also relates to the application of the latices in the field of chemistry or of biology, especially for the methods of diagnostics, of separation and of calibration. This is the case especially with biological assay methods which are well known to a person skilled in the art, for binding or immobilizing biologically active substances (proteins, antibodies, enzymes, antigens and medications) by adsorption or coupling.

These microspheres can be employed as carrier in diagnostic tests (RIA, or radioimmunological assay, IRMA, or immunoradiometric assay, EIA, or enzyme immuno assay and ELISA, or enzyme linked immunosorbent assay, agglutination) or for nuleic [sic] acid probes, as enzyme catalyst in biotechnology or as cell culture medium.

Of course, bearing in mind their very small size, the microspheres and the corresponding aqueous dispersions are also capable of being advantageously employed in fields which are more industrial, of the coating industry type, like paint, adhesive coating, textile, paper etc.

The invention is now illustrated by the following examples which are described solely by way of illustration. The general operating procedure which is common to all these examples involves the following reactants:

- organic alcoholic solvent,
- monomer(s)
- poly(vinyl pyrrolidone),
- sodium dioctylsulfosuccinate,
- ferrofluid
- 2,2'-azobis(isobutyronitrile) as initiator.

The operating conditions correspond to the following characteristics:

reaction in nitrogen atmosphere at a polymerization temperature of 70° for several hours, approximately 20 hours.

In the first place the initiator is dissolved in the monomer (s) (solution A), stirring is applied and the ferrofluid is added next.

The poly(vinyl pyrrolidone) and the sodium dioctylsulfosuccinate are dissolved in the solvent and stirring is applied for several hours (solution B).

Solution B is introduced into a reactor, is heated to 60° C. for 40 minutes, this temperature is maintained for several minutes and solution A is added.

The temperature increases to 70° C. and the polymerization takes place during the period indicated above.

The microspheres are then resuspended after separation by the action of a magnetic field followed by replacement of the supernatant with distilled water to which 0.5% of SDS has been added.

The latices obtained in the examples below have been characterized from the viewpoint of particle size with the aid of the Cilas 850 laser particle size analyser marketed by Cilas and from the viewpoint of determination of the surface functional groups by conductimetric assay of the acid groups.

EXAMPLE 1

The solution includes, by weight:

| | | |
|---|---|---|
| 2-Methylpropanol | = 34 g | |
| Ethanol | = 34.2 g | |
| Styrene | = 15 g | |
| Ferrofluid | = 12 g | { 7 g styrene<br>3.6 g pigment<br>1.44 g Gafac RE 610* |
| Poly (vinyl pyrrolidone) (PVP) (stabilizer) of molecular weight 40 000 | = 4 g | |
| Sodium dioctylsulfosuccinate | = 0.6 g | |
| 2,2'-Azobis (isobutyronitrile) initiator (AIBN) | = 0.4 g. | |

Gafac RE 610* is a mixture of phosphoric mono- and diesters of ethoxylated alkylaryl derivatives, marketed by Rhône-Poulenc.

The measurements carried out show that the microspheres have a mean diameter of 0.87 micrometers with a standard deviation of 15%.

The iron content is 11.2% and the number of carboxyl functional groups is 25 microequivalents per gram of dry microspheres.

EXAMPLE 2

| | |
|---|---|
| 2-Methylpropanol | = 34 g |
| Ethanol | = 34.3 g |
| Styrene | = 22 g |
| Ferrofluid | = 5 g |
| PVP of molecular weight 40 000 | = 4 g |
| Sodium dioctylsulfosuccinate | = 0.3 g |
| AIBN | = 0.38 g. |

The measurements carried out show that the microspheres have a mean diameter of 1.07 micrometers with a standard deviation of 15%. The iron content is 4.7%. A photograph enclosed herewith at a magnification of 5000 times shows the remarkable homogeneity of the microspheres obtained (FIG. 1).

EXAMPLE 3

The following solution is produced:

| | |
|---|---|
| 2-Methylpropanol | = 34 g |
| Ethanol | = 34 g |
| Styrene | = 7 g |
| Ferrofluid | = 20 g |
| PVP of molecular weight 40 000 | = 4 g |
| Sodium dioctylsulfosuccinate | = 0.3 g |
| AIBN | = 0.38 g. |

Figure 2:
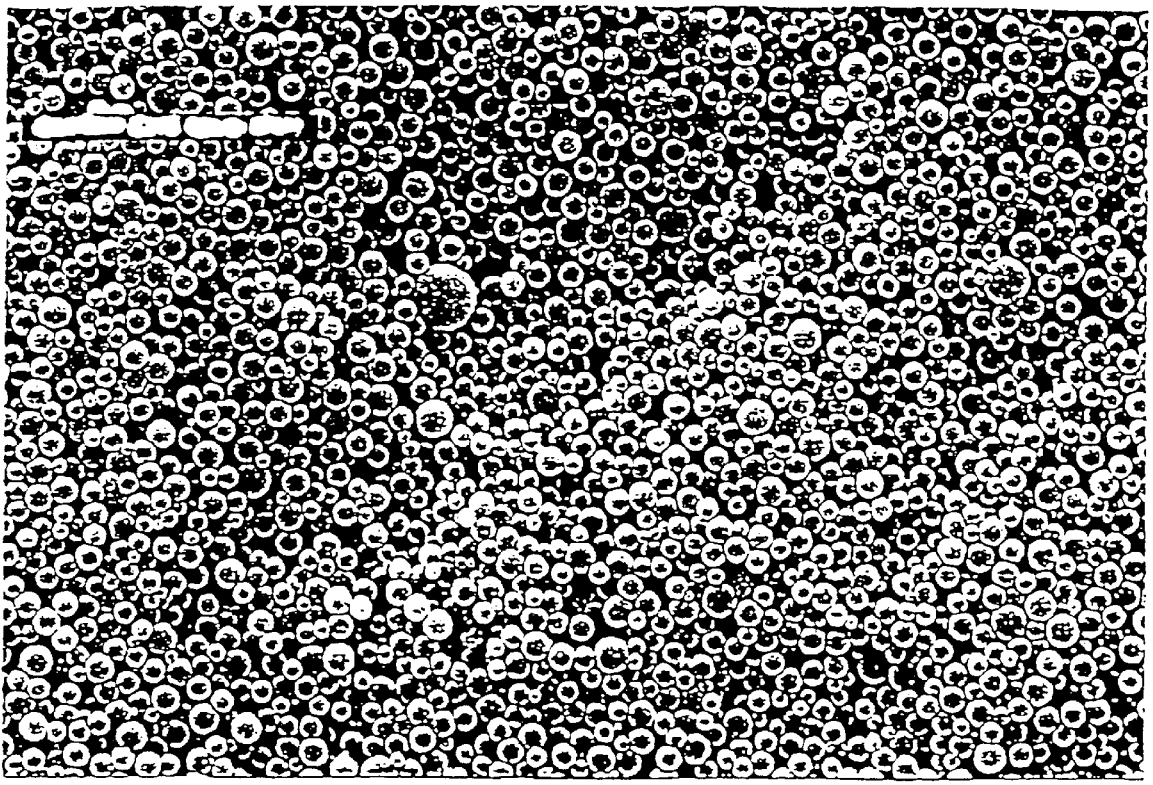

The measurements carried out show that the microspheres have a mean diameter of 1.15 micrometers with a standard deviation of 10%. The iron content is 19%. The photograph enclosed herewith at a magnification of 5000 times shows the remarkable homogeneity of the microspheres obtained (FIG. 2).

EXAMPLE 4

The following solution is produced:

| | |
|---|---|
| 2-Methylpropanol | = 34 g |
| Ethanol | = 34 g |
| Styrene | = 15 g |
| Ferrofluid | = 12 g |
| PVP of molecular weight 360 000 | = 2.5 g |
| Sodium dioctylsulfosuccinate | = 0.3 g |
| AIBN | = 0.4 g. |

Figure 3:
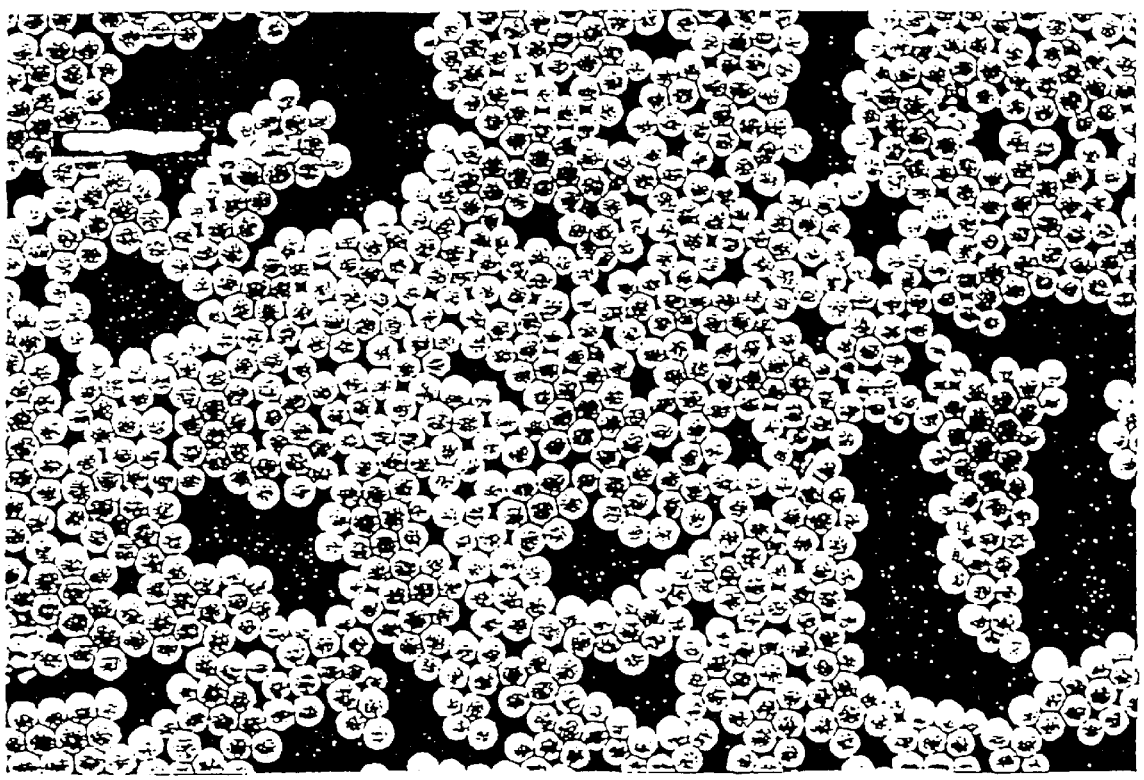

The measurements carried out show that the microspheres have a mean diameter of 1.3 micrometers with a standard deviation of 5%. The iron content is 12%. A photograph enclosed herewith at a magnification of 5000 times shows the remarkable homogeneity of the microspheres obtained (FIG. 3).

EXAMPLE 5

The following solution is produced:

| | |
|---|---|
| 2-Methylpropanol | = 34 g |
| Ethanol | = 34 g |
| Styrene | = 15 g |

-continued

| | |
|---|---|
| Ferrofluid | = 12 g |
| PVP of molecular weight 360 000 | = 1.5 g |
| Sodium dioctylsulfosuccinate | = 0.3 g |
| AIBN | = 0.4 g. |

Figure 4:
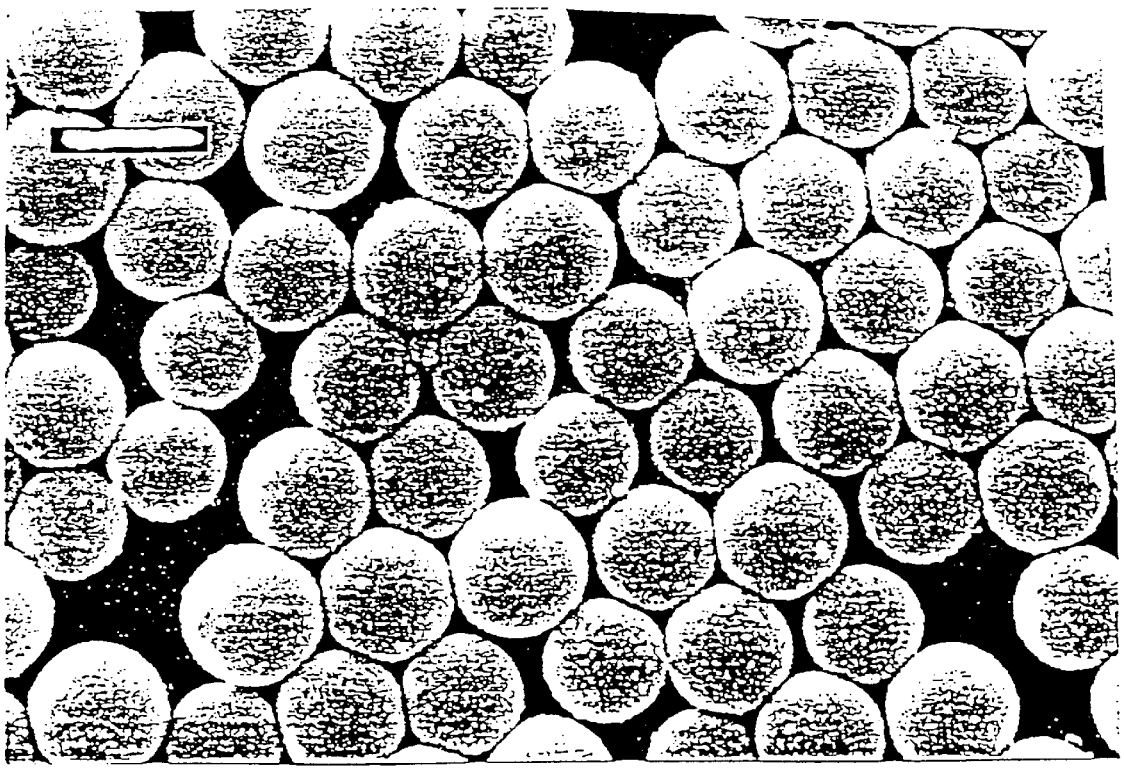

The measurements carried out show that the microspheres have a mean diameter of 1.4 micrometers with a standard deviation of 5%. The iron content is 12.5%. A photograph enclosed herewith at a magnification of 20,000 times shows the remarkable homogeneity of the microspheres obtained (FIG. 4).

Of course, the invention is not limited to the embodiments described in the present application but extends to all the alternative forms which a person skilled in the art is capable of producing in the light of the teaching of the present application.

We claim:

1. Process of preparation of a calibrated monodisperse latex of magnetizable microspheres which have a standard deviation smaller than or equal to 15% and which are made up of a hydrophobic polymer matrix, and of magnetizable fillers, the microspheres having a calibrated particle size distribution, a size of between approximately 0.5 and 5 micrometers, and the polymer matrix being made up of polymers derived from at least one vinyl monomer, by dispersion polymerization, characterized (a) in that an organic solution, substantially free of water, including at least one polymerizable vinyl monomer, an organic solvent, magnetizable fillers in ferrofluid form, and a stabilizing system for the polymer formed is reacted in the presence of an organosoluble polymerization initiator and (b) in that the monodisperse latex of magnetizable microspheres is recovered.

2. Process of preparation according to claim 1, characterized in that the solvent is polar.

3. Process of preparation according to claim 2, characterized in that the solvent is an alcoholic or ether solvent or a water-alcohol or ether-alcohol mixture.

4. Process of preparation according to claim 2, characterized in that the monomer is selected from the group consisting of vinylaromatic monomers, acrylic and methacrylic acid, $C_1$–$C_{10}$ alkyl acrylates and methacrylates, hydroxyalkylacrylates and methacrylates, acrylamide and methacrylamide, vinylmonomers which have an electron attracting group, and as comonomers, isoprene and butadiene.

5. Process of preparation according to claim 2, characterize in that the stabilizing system is a polymer selected from the group consisting of poly(vinyl pyrrolidone), acrylic and methacrylic homopolymers, and random and block copolymers of (i) monomers selected from the group consisting of styrene, styrene derivatives, and butadiene and (ii) monomers selected from the group consisting of methacrylic acid and acrylic acid.

6. Process of preparation according to claim 1, characterized in that the solvent is apolar.

7. Process of preparation according to claim 6, characterized in that the solvent is selected from the group consisting of hexane and cyclohexane.

8. Process of preparation according to claim 6, characterized in that the monomer is selected from the group consisting of alkyl acrylates and methacrylates, styrene derivatives, and dienes.

9. Process of preparation according to claim 6, characterized in that the stabilizing system is a polymer selected from the group consisting of (a) polyacrylates and methacrylates and (b) block and random copolymers of (i) monomers selected from the group consisting of styrene derivatives, butadiene derivatives, and vinyl esters and (iii) monomers selected from the group consisting of acrylate and methacrylate derivatives and alkylsiloxanes.

10. Process of preparation according to claim 1 characterized in that the solution includes an ionic costabilizer.

11. Process of preparation according to claim 10 characterized in that the costabilizer is selected from the group consisting of sodium dioctylsulfosuccinate and methyltricaprylammonium chloride.

12. Process of preparation according to claim 1, characterized in that the polymerization initiator is selected from the group consisting of 2,2'-azobis(isobutyronitrile), 4,4'-azobis(4-cyanopentanoic acid), 2,2'-azobis(2-methylbutyronitrile), benzoyl peroxide, and 2,2'-azobis(2,4-dimethyl-valeronitrile).

13. Process of preparation according to claim 1, characterized in that the solution includes, in parts by weight:

| | |
|---|---|
| organic solvent | 45 to 90 |
| monomer | 5 to 30 |
| ferrofluid | 2 to 30 |
| stabilizing system | 2 to 10 |
| costabilizer | 0.1 to 1 |
| initiator | 0.1 to 1. |

* * * * *